United States Patent
Hwang et al.

(10) Patent No.: US 10,441,540 B2
(45) Date of Patent: Oct. 15, 2019

(54) LIPOSOMAL LUPEOL ACETATE AND THE USE THEREOF IN PREPARING DRUGS FOR RHEUMATOID ARTHRITIS

(71) Applicant: NATIONAL YANG-MING UNIVERSITY, Taipei (TW)

(72) Inventors: Jeng-Jong Hwang, Taipei (TW); Wei-Hsun Wang, Taichung (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 870 days.

(21) Appl. No.: 14/536,336

(22) Filed: Nov. 7, 2014

(65) Prior Publication Data
US 2015/0258025 A1  Sep. 17, 2015

(30) Foreign Application Priority Data
Mar. 14, 2014 (TW) .............................. 103109435 A

(51) Int. Cl.
*A61K 9/127* (2006.01)
*A61K 31/57* (2006.01)
*A61K 45/06* (2006.01)
*A61K 31/56* (2006.01)

(52) U.S. Cl.
CPC ............ *A61K 9/127* (2013.01); *A61K 9/1271* (2013.01); *A61K 31/56* (2013.01); *A61K 31/57* (2013.01); *A61K 45/06* (2013.01)

(58) Field of Classification Search
CPC ..................................................... A61K 9/127
See application file for complete search history.

(56) References Cited

U.S. PATENT DOCUMENTS

| 5,356,633 A * | 10/1994 | Woodle | A61K 9/1271 424/423 |
| 2004/0180082 A1* | 9/2004 | Kang | A61K 31/19 424/450 |
| 2006/0025389 A1* | 2/2006 | Gibson | A61K 31/56 514/169 |
| 2007/0281047 A1* | 12/2007 | Henry | A61K 8/97 424/776 |
| 2012/0177754 A1* | 7/2012 | Blain | A61K 36/324 424/725 |

OTHER PUBLICATIONS

Akihisa et al., "Anti-Inflammatory and Chemopreventive Effects of Triterpene Cinnamates and Acetates from Shea Fat", Journal of Oleo Science, 2010, No. 59 (6), pp. 273-280.
(Continued)

*Primary Examiner* — Gollamudi S Kishore
(74) *Attorney, Agent, or Firm* — WPAT, PC

(57) ABSTRACT

The present invention relates to a liposomal lupeol acetate (Lipo-LA) and its use in the treatment or prevention of rheumatoid arthritis (RA). The liposomal lupeol acetate of the present invention especially inhibits inflammatory responses and osteoclast generation (osteoclastogenesis) in the progression of rheumatoid arthritis (RA) at a half dose of the un-capsulated lupeol acetate, which may significantly reduce the incidence of RA and improve the therapeutic efficacy of lupeol acetate.

5 Claims, 18 Drawing Sheets
(5 of 18 Drawing Sheet(s) Filed in Color)

(56) References Cited

OTHER PUBLICATIONS

Lucetti et al., "Anti-inflammatory effects and possible mechanism of action of lupeopl acetate isolated from Himatanthus drasticus (Mart.) Plumel", Journal of Inflammation, 2010, 7:60, 11 pages.
Breedveld, "Current and future management approaches for rheumatoid arthritis", Arthritis Research, Mar. 27, 2002, vol. 4 Suppl 2, pp. s16-s21.
Siddique et al., "Beneficial health effects of lupeol triterpene: A review of preclinical studies", Life Sciences, 2011, No. 88, pp. 285-293.
Saleem, "Lupeol, A Novel Anti-inflammatory and Anti-cancer Dietary Triterpene", Cancer Lett., 285(2), Nov. 28, 2009, pp. 109-115.

* cited by examiner

LIPOSOMAL LUPEOL ACETATE AND THE USE THEREOF IN PREPARING DRUGS FOR RHEUMATOID ARTHRITIS

BACKGROUND OF THE INVENTION

Technical Field of the Invention

The present invention relates to liposomal lupeol acetate (Lipo-LA) and its use in the treatment or prevention of rheumatoid arthritis (RA). Especially, of the present invention relates to a method for preventing and/or treating inflammation in the progression of rheumatoid arthritis (RA) by inhibiting osteoclast generation with the administration of the liposomal lupeol acetate.

Background

Rheumatoid arthritis (RA) is a chronic autoimmune disorder that basically results in a symmetry, multi-joint, small joint inflammatory disease that may affect many tissues and organs, but principally attacks flexible (synovial) joints, and cause the disintegration of articular cartilage and bone injuries. It can be a swelling and painful condition, which can lead to joint deformity at late stage and substantial loss of functioning and mobility.

Rheumatoid arthritis is closely correlated with excessive activation of macrophages. The release of cytokines due to macrophage activation will attract more immune cells to infiltrate, result in more severe inflammatory response. Macrophages may differentiate into osteoclasts and lead to bone erosion in the joint cavity, which is the main reason for the progression of RA.

The major pharmaceuticals used in clinical treatment of RA are steroids, non-steroid anti-inflammation drugs, and certain biological agents against cytokine, such as TNF-α blockers, anti-IL-1β, anti-IL-6 antibodies, and the like (Breedveld F C. *Arthritis Res* 2002, 4(2):27). Such therapeutic agents are not only expensive, but also possess certain degree of side effects. The most commonly used agent is methotrexate, which is usually the first treatment to improve symptoms, decrease joint damage, and improve overall functional abilities. However, the pathogenesis of RA is not very clear so far, and known therapeutic drugs and biologics for clinical use do not effectively cure rheumatoid arthritis and will produce side effects. Therefore, it is necessary to find a more effective and safe drug for the treatment of rheumatoid arthritis.

Lupeol acetate (LA), a type of triterpene, is an ingredient in the extraction of Shea nut, and existed in the mango, cabbage and green pepper. Lupeol acetate has a chemical structure similar to sterols, and has been known with capability of anti-inflammation, antioxidation, anticancer and immunomodulation (see, Akihisa T et al., *J Oleo Sci* 2010, 59(6):273-280; Saleem M. *Cancer Lett* 2009, 285(2):109-115; Siddique H R, Saleem M. *Life Sci* 2011, 88(7-8):285-293). It is also demonstrated that LA can effectively mitigate the inflammatory condition induced by carrageenan in mice (Lucetti D L et al. *J Inflamm* 2010, 7(60)).

In addition, US Patent Application no. 20120177754 has disclosed extraction of lupeol acetate from *Boswellia frereana*, and the significant therapeutic effect of lupeol acetate in inhibiting inflammation and treatment of rheumatoid arthritis, but the animal model experiments show that long-term use of high doses (100 mg/kg, 12 days) is necessary for rheumatoid arthritis treatment in mice even a highly pure extract of natural lupeol acetate (95%) is used in the therapy.

Liposome is a spheroid formed by phospholipid bilayers, in which a hydrophilic drug may be coated in the inner hydrophilic cavity, lipophilic drugs may be carried by interspersing among the lipids. In one embodiment of the invention, two kinds of lipids egg phosphatidylcholine (EPC) and polyethylene glycol-distearoylphosphatidylethanolamine (PEG-DSPE) were used. EPC is a kind of phospholipid extracted from egg, and PC is the major component of cell membrane. Although PC is widespread in the organism, it is a less stable factor in lipid layer for that PC has an unsaturated fatty acid long-chain at the lipophilic terminus, in which the unsaturated bonds will confer a greater bending on the carbon chain, resulting in unclose integration with the adjacent phospholipids in the arrangement of lipid bilayer structure. While PEG-DSPE is a more stable lipid than PC for having no interference from the unsaturated bond, so it can be arranged closely to the adjacent phospholipid and form a more compact lipid layer.

Therefore, the present invention contemplates to prepare lupeol acetate liposomes for achieving effects of better suppression of inflammation and bone erosion by using the characteristics of liposome that has a longer in vivo residence time for not being susceptible to metabolism, and may cause larger space for accumulation between the vessel wall in the target treating area.

SUMMARY OF INVENTION

Based on the purpose above, the present invention provides a liposomal lupeol acetate (Lipo-LA) liposome to reduce half dose of uncoated lupeol acetate for alleviating or preventing the inflammatory swelling and joint deformation in the progression of rheumatoid arthritis (RA).

Accordingly, in one aspect, the present invention relates to a pharmaceutical composition for treating or preventing osteoclastogenesis in rheumatoid arthritis (RA) progression, comprising a liposomal lupeol acetate (Lipo-LA) liposome and a pharmaceutically acceptable vehicle, diluent or excipient, wherein the liposomal lupeol acetate liposome comprises lupeol acetate and a diphospholipid layer consisting of a lipophilic lipid layer and a hydrophilic phosphate layer.

As used herein, the term "liposomal lupeol acetate" and "lupeol acetate liposome" are interchangeable, and may be represented as "Lipo-LA" through the description of Specification and Claims.

In one embodiment of present invention, the lupeol acetate is interspersed in the lipophilic lipid layer of the lipid bilayer.

In certain embodiments of present invention, the diphospholipid layer is constructed by a phosphatidylcholine (PC) and polyethylene glycol-distearoylphosphatidylethanolamine (PEG-DSPE). In one embodiment of present invention, the phosphatidylcholine comprises egg phosphatidylcholine (EPC). Preferably, the molecular ratio of the phosphatidylcholine (PC) and polyethylene glycol-distearoylphosphatidylethanolamine (PEG-DSPE) in the diphospholipid layer of liposome is 20:1 to 35:1, more preferably is 25:1 to 30:1, and most preferably is 30:1.

In some embodiments of present invention, the pharmaceutical composition further comprises a steroid anti-inflammatory agent. In that case, the liposomal lupeol acetate included in the pharmaceutical composition is used to reduce osteoporosis caused by the steroid anti-inflammatory agent.

In another aspect, the present invention relates to a method treating or preventing an osteoclastogenesis associated condition by administering the pharmaceutical composition of claim 1, wherein the osteoclastogenesis is suppressed by lupeol acetate.

In one embodiment of present invention, the osteoclastogenesis associated condition is rheumatoid arthritis (RA). In another embodiment of present invention, the osteoclastogenesis associated condition is osteoporosis. In a further embodiment of present invention, the osteoporosis is a sterol anti-inflammatory agent triggered osteoporosis.

In certain embodiments, the osteoclastogenesis is suppressed by inhibiting a differentiation of osteoclast from macrophage.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows the differentiation of osteoclast from macrophage under the culture condition containing 100 ng/ml of RANKL (receptor of activation of NF-κB ligand) and drug treatment. The cells were stained with tartrate-resistant acid phosphatase (TRAP) and observed by microscopy to assure the differentiation of osteoclast after the cultivation of five days (Bar=200 μm). FIG. 3B shows the expression of NFATc1 (nuclear factor of activated T cell, cytoplasmic 1) analyzed by real-time Q-PCR. The use of 5 nM NF-κB inhibitor also reduces the expression of NFATc1. ***$p<0.001$, in comparison to LPS group; #$p<0.05$ and ###$p<0.001$, the comparison between 40 μM Lipo-LA and 80 μM Lipo-LA.

FIG. 4A shows the analytic results and quantitative evaluation of the expression of CD80/CD86 co-stimulator in macrophage. FIGS. 4B, 4C and 4D are the analytic results of TNF-α, IL-1β and IL-6 release with ELISA, respectively, which is performed in the culture supernatants collected after the treatment of 40 μM Lipo-LA or 80 μM Lipo-LA for 1 hour prior to the stimulation of 1 μg/ml LPS for another 24 hours. ***$p<0.001$, in comparison to LPS group; ##$p<0.01$ and ###$p<0.001$, the comparison between 40 μM Lipo-LA and 80 μM Lipo-LA; n=3 in each group for a triplicate experiment.

FIG. 6A shows the changes in body weight of mice after giving 100 mg/kg LA, indicating no toxic effects on the treated animal FIG. 6B shows the incidence of arthritis in each group, indicating decreased incidence percentages in the 100 mg/kg LA and 50 mg/kg Lipo-LA treated mice and no significant difference between the animals in these two groups. FIG. 6C shows the arthritis scores in each group (the highest score is 16 points for every mouse), indicating the significantly less scores in 100 mg/kg LA and 50 mg/kg Lipo-LA treated mice than those of RA group. FIG. 6D shows the paw thickness measured with an electronic vernier, indicating that the swelling of paw is more significant in normal control group and RA group than in 100 mg/kg LA and 50 mg/kg Lipo-LA treated mice.

In FIGS. 7C and 7D, legs of mice were removed and ground for obtaining the extract of cytosol and nuclear proteins used in the Western blotting and electrophoretic mobility shift assay (EMSA), respectively. #$p<0.05$, the comparison between RA vs. 50 mg/kg Lipo-LA, and 100 mg/kg LA vs. 50 mg/kg Lipo-LA groups, respectively. In this study, 100 mg/kg LA and 50 mg/kg Lipo-LA were used, respectively.

In FIG. 8A, mice were sacrificed at the end of the animal experiment (day 43), and the legs was removed for the immunohistochemistry (IHC) of TNF-α and IL-1β and H&E staining. The arrows in H&E images indicate the position of articular cavity. There is significant accumulation of TNF-α and IL-1β appeared in the RA group. FIG. 8B shows the similar therapeutic efficacies of 100 mg/kg LA and 50 mg/kg Lipo-LA as presented in H&E staining.

DETAILED DESCRIPTION OF THE INVENTION

The other characteristics and advantages of the present invention will be further illustrated and described in the following examples. The examples described herein are using for illustrations, not for limitations of the invention.

Preparation of Liposomal Lupeol Acetate (Lipo-LA)

Figure 1:
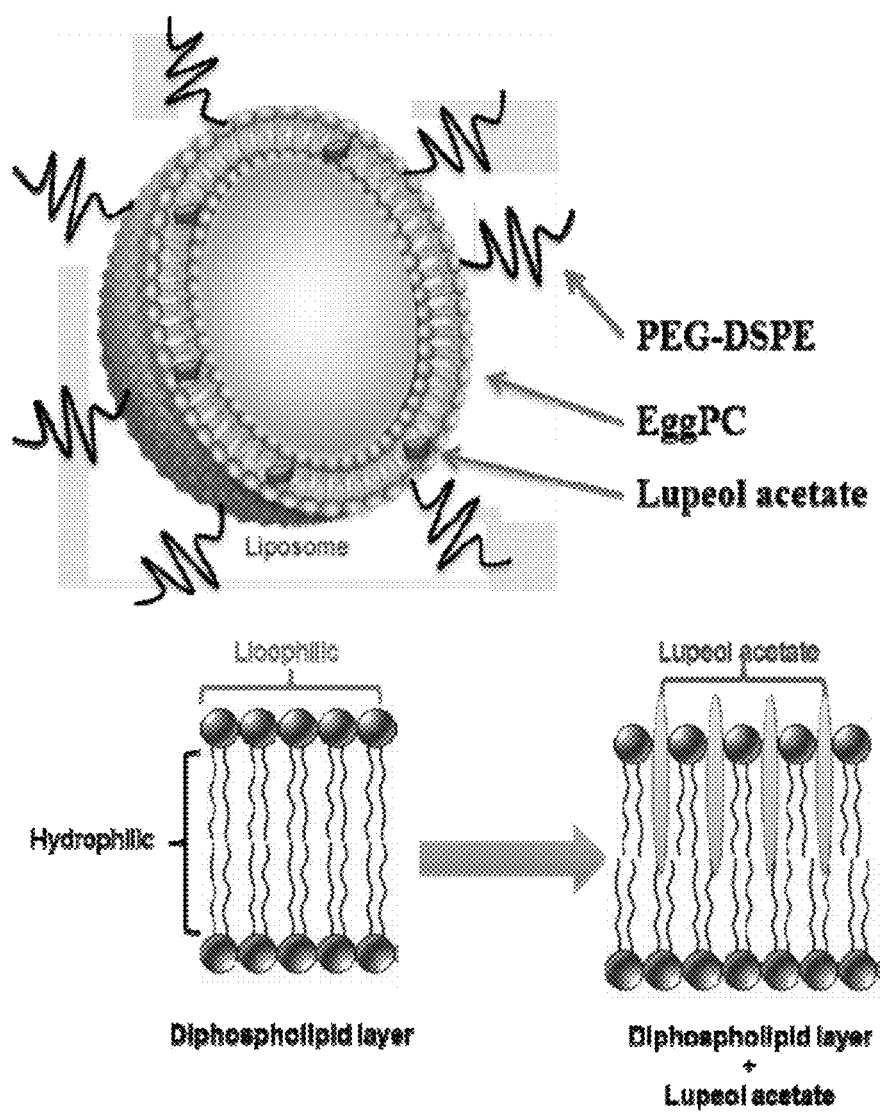
FIG. 1 shows a schematic diagram of the molecular structure of liposomal lupeol acetate (Lipo-LA). Lupeol acetate is interspersed in the lipid lipophilic lipid layer of the diphospholipid layer.

The liposomal lupeol acetate (Lipo-LA) of present invention has a molecular structure as shown in FIG. 1. In the construct of liposomal lupeol acetate, lupeol acetate is interspersed between the lipids of lipid bilayer by its hydrophobic properties. The composition of the liposomal lupeol acetate comprises: egg phosphatidylcholine (EPC), polyethylene glycol-distearoylphosphatidylethanolamine and lupeol acetate, at the molar ratios of 30:1:2.1 μM, which are dissolved in small amount of chloroform. The mixed solution is then rotated in a rotary vacuum concentrator at 60° C. until the chloroform is completely removed, and an evenly distributed thin layer of lipid is obtained in the draining procedure.

A 0.9% sodium chloride solution is added to dissolve the lipid layer. The solution is first filtered through 0.4 μm filter membrane for six times, then followed by 0.2 μm filter membrane for ten times by using a high-pressure shaping to obtain lupeol acetate liposomes with particle size less than 0.2 μm. The liposomal lupeol acetate prepared by the method of this example has particle size in range of 90±10 nm, and particle charge in the range of ±10 mV, 5-10% PEG.

Cytotoxicity of Liposomal Lupeol Acetate (Lipo-LA) to the RAW264.7 Cell Line

RAW 264.7 cells (a mouse leukaemic monocyte macrophage cell line) were treated with solutions containing liposomal lupeol acetate (10、20、40、80 μM) and NF-kB inhibitor QNZ (2.5、5、7.5、10 nM), respectively, for 24 hours, then the viability was analyzed by MTT method, comparing to the results of the control group.

$5 \times 10^4$ RAW264.7 cells/well were seeded in 96-well culture dishes, and treated with directed concentration of liposomal lupeol acetate and QNZ for 24 hours after the 24-hr attachment. After removing the culture medium, 100 μl of 0.5 mg/ml MTT solution was added, and the cells were incubated at 37° C. for 4 hours. The mitochondrial enzyme (succinate dehydrogenase, SDH) in living cells will react with tetrazolium bromide in the MTT solution and form formazan blue-purple crystals. The MTT solution was removed and 200 μl DMSO was added to dissolve the blue-purple crystal, and then the O.D. (optical density) value was read under wavelength of 570 nm on an ELISA reader (TECAN Sunrise, USA). The relative cell viability is calculated by comparing the absorbance value of drug treated group with that of the control group (setting the value of control group as 100%).

Figure 2A:
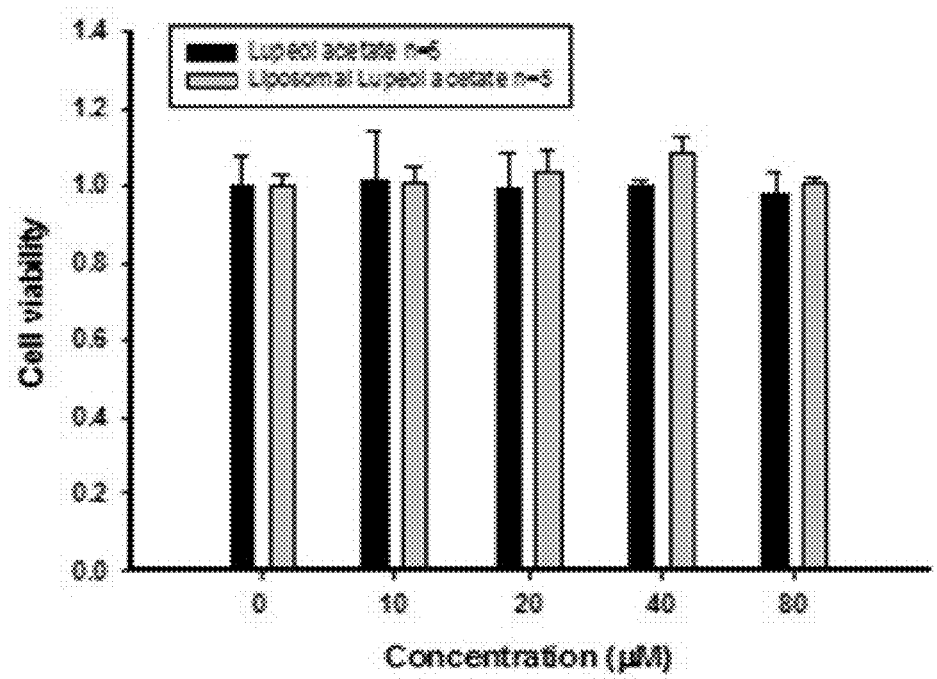
FIGS. 2A-2B show the cell viability of RAW 264.7 cells after the drug treatment of 0-80 μM lupeol acetate (LA) or liposomal lupeol acetate (Lipo-LA) for 24 hours in FIG. 2A; and 0-10 nM NF-κB activation inhibitor 481406 (QNZ) for 24 hours in FIG. 2B analyzed by MTT (3-(4,5-cimethylthiazol-2-yl)-2,5-diphenyl tetrazolium bromide). The experimental results are compared to the respective control groups, which resultant value is set to 1.
Figure 2B:
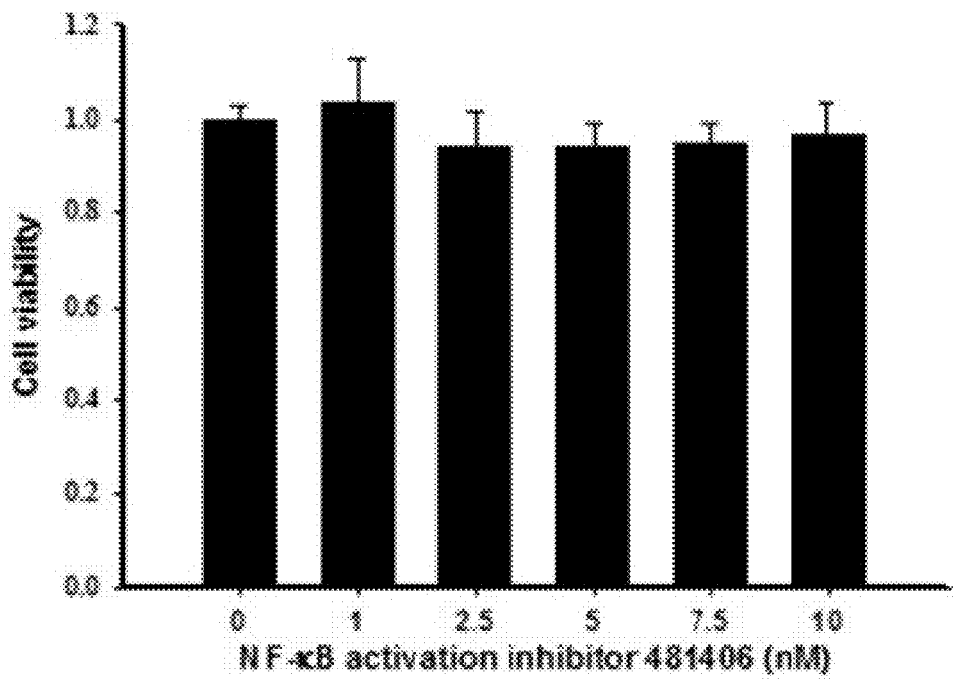

From the analytic results shown in FIG. 2A, Lipo-LA has no cytotoxic effects on RAW264.7 cells as increasing concentrations. FIG. 2B shows that use of QNZ (NF-κB activation inhibitor, 481406) does not cause significant cell death, so we chose 80 μM lipo-LA or 80 μM LA, and 5 nM QNZ for the subsequent experiments.

Inhibitory Effects of Liposomal Lupeol Acetate (Lipo-LA) on the Formation of Osteoclasts Induced by RANKL The generation and metabolism of bones are kept in a state of dynamic equilibrium, and the destruction of this equilibrium will cause the damage of bones. In rheumatoid arthritis, there is excessive osteoclast formation occurred and resulting in the over-erosion of bone.

To evaluate the effects of the liposomal lupeol acetate (Lipo-LA) of present invention on the suppression of rheumatoid arthritis, we firstly analyze the differentiation of osteoclasts from certain cells using the tartrate-resistant acid phosphatase (TRAP) staining method. The TRAP staining is used to detect the internal acid phosphatase activity of leukocytes in a blood, bone or tissue sample. Because osteoclasts contain acid phosphatase, we can use this staining method to determine the formation of osteoclast cells.

After removing the supernatant of culture, the cells are rinsed with PBS for two times, and then fixed with 3.7% paraformaldehyde for 1 hour. The fixed cells are washed with PBS. The Acid Phophatase Leukocyte kit (TRAP stain, Cat. 387-A, Sigma-Aldrich, USA) is used in the TRAP staining and the method is briefly described as follow. Before staining, the temperature of ddH$_2$O used for adjuvant preparation is confirmed to be 37° C. The Fast Garnet GBC base and sodium nitrite solution at equal volumes are uniformly mixed for 30 seconds and incubated at room temperature for at least two minutes.

Then following the procedures described in the instruction manual, a staining agent is prepared by adding a well-mixed solution of 1 ml Fast Garent GBC base, 0.5 ml Naphthol AS-BI phosphate solution, 2 ml acetate solution and 1 ml tartrate solution to 45 ml of 37° C. ddH$_2$O. The staining agent is uniformly mixed and added to each well of 96-well plate at 100 μl aliquot, and then placed in a 37° C. dark incubator for one hour. After the reaction, the 96-well plate is wetted by ddH$_2$O, and stained with a hematoxylin solution included in the kit for ten minutes, then rinsed with tap water and air dried naturally. Finally, the osteoclast differentiation is observed under a microscope, the nucleus of each cell must be greater than three nuclei for being identified as osteoclast.

Figure 3A:
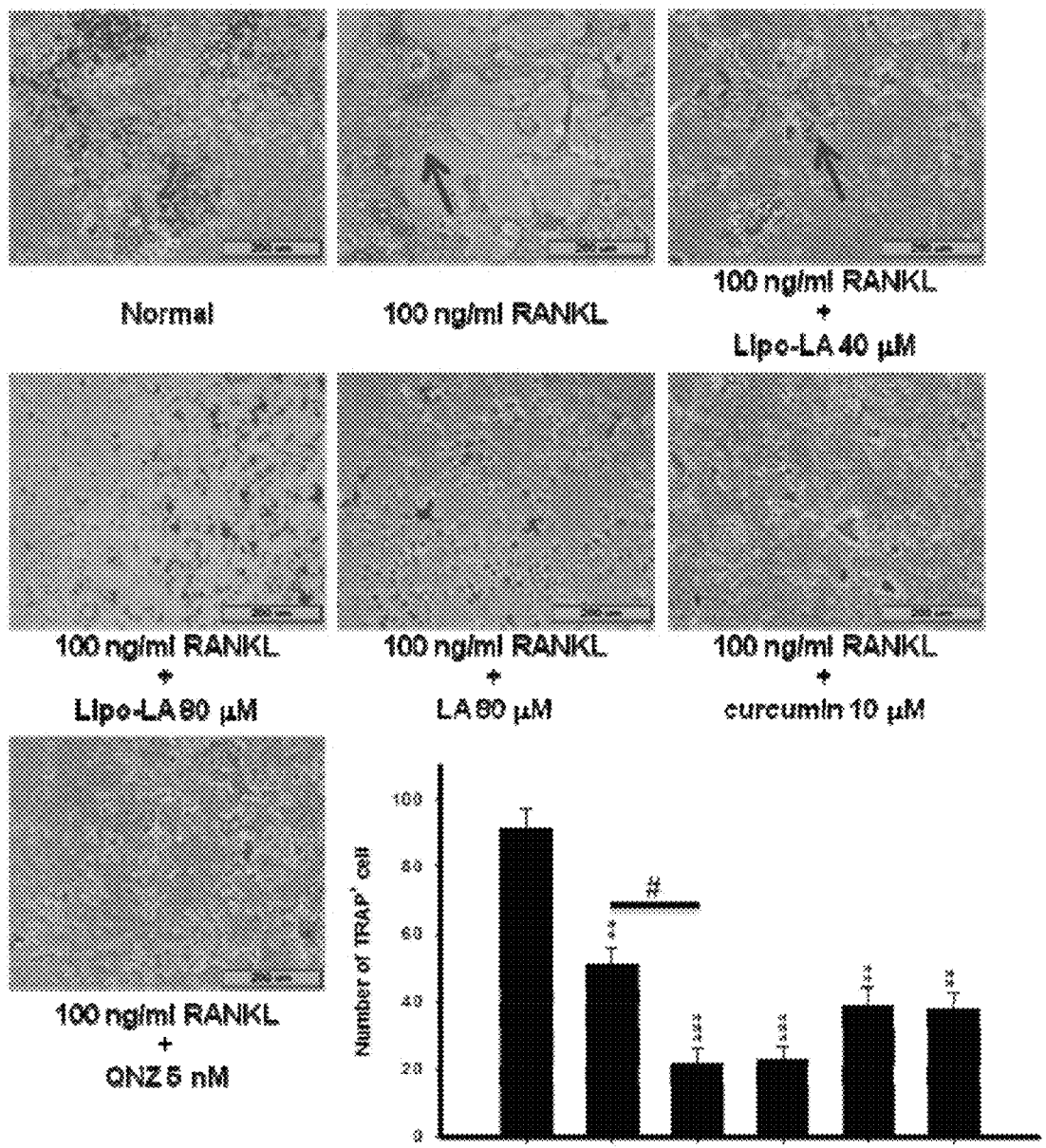
FIGS. 3A-3B show the inhibitory effects of lupeol acetate (LA) and liposomal lupeol acetate (Lipo-LA) on RANKL-inducing osteoclastogenesis by regulating NF-κB, using 10 μM curcumin as the positive control.

In this experiment, curcumin is chosen as the positive control for it is known to have similar effects of anti-cancer, anti-inflammatory and anti-rheumatoid arthritis disease to lupeol acetate, and both are natural substance. As shown in FIG. 3A, macrophages differentiate into osteoclasts under the stimulation of receptor of activation of NF-κB ligand (RANKL); and an indeed decrease in the macrophage differentiation into osteoclasts is observed after administration of drugs.

Figure 3B:
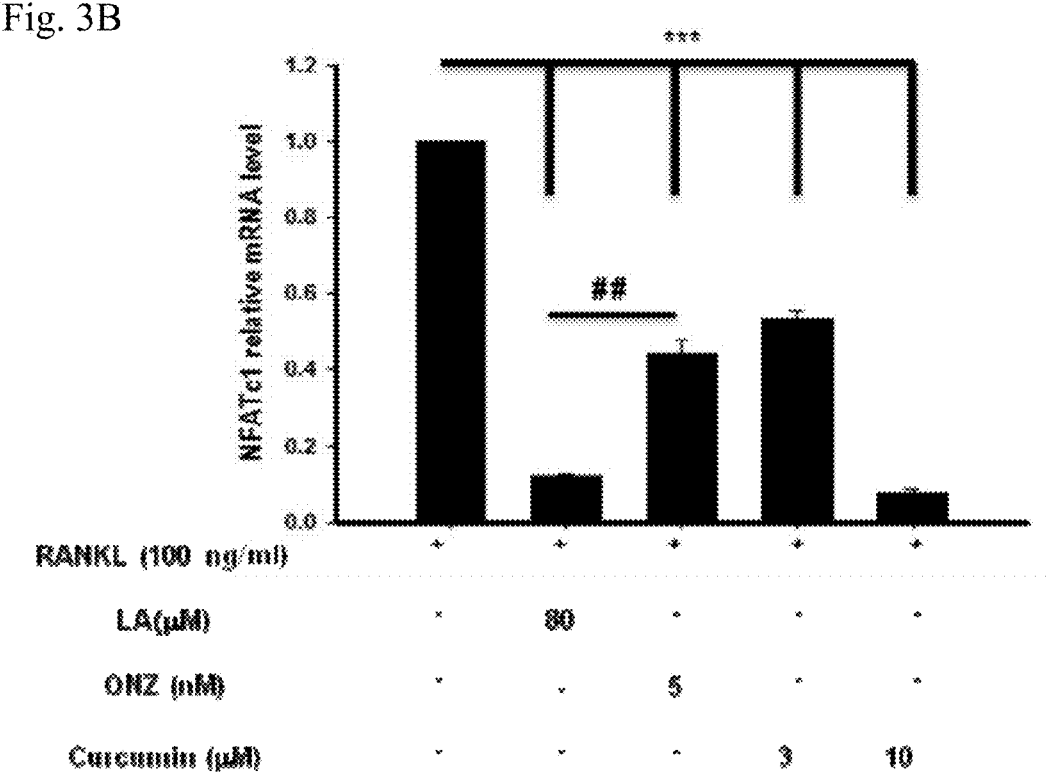
Figure 3B:
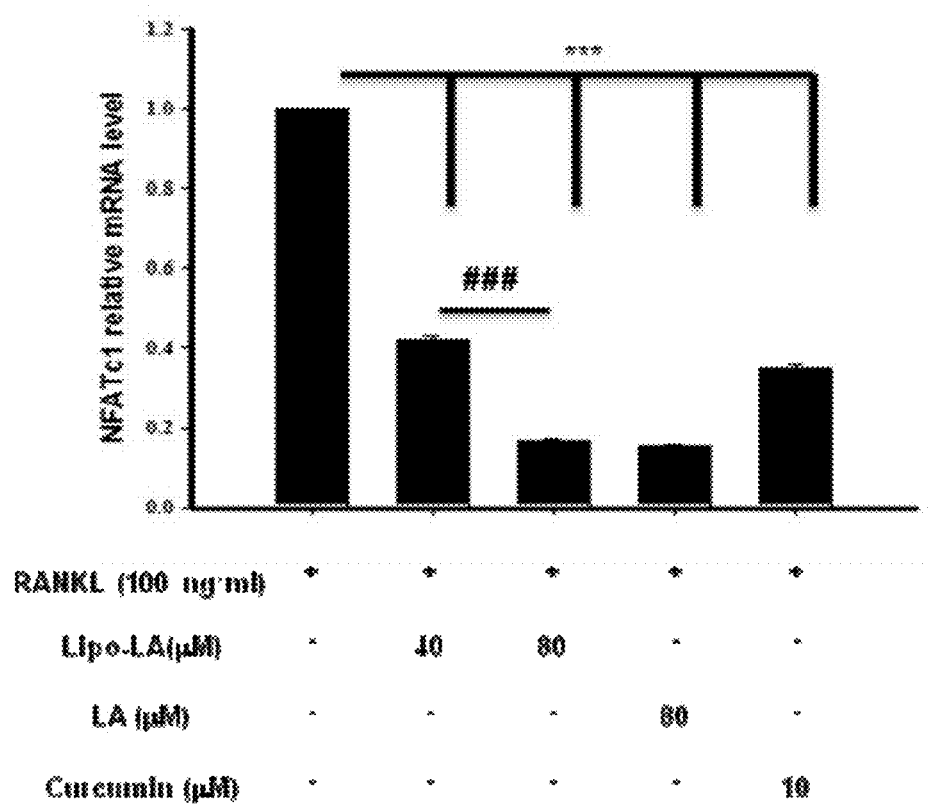
Figure 4A:
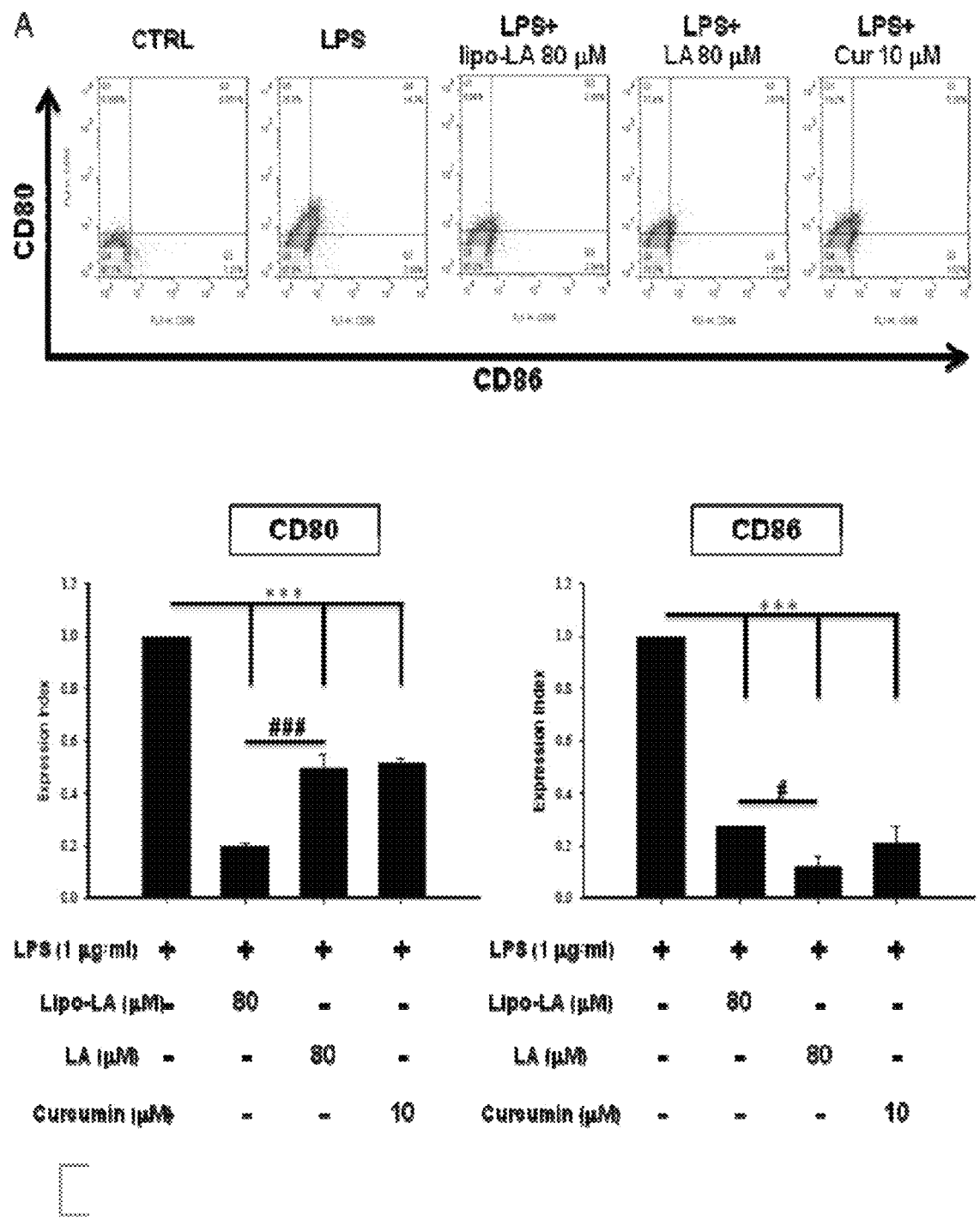
FIGS. 4A-4D show the inhibitory effects of liposomal lupeol acetate (Lipo-LA) on the LPS-stimulating release of co-stimulators and inflammatory factors from macrophage.
Figure 4B:
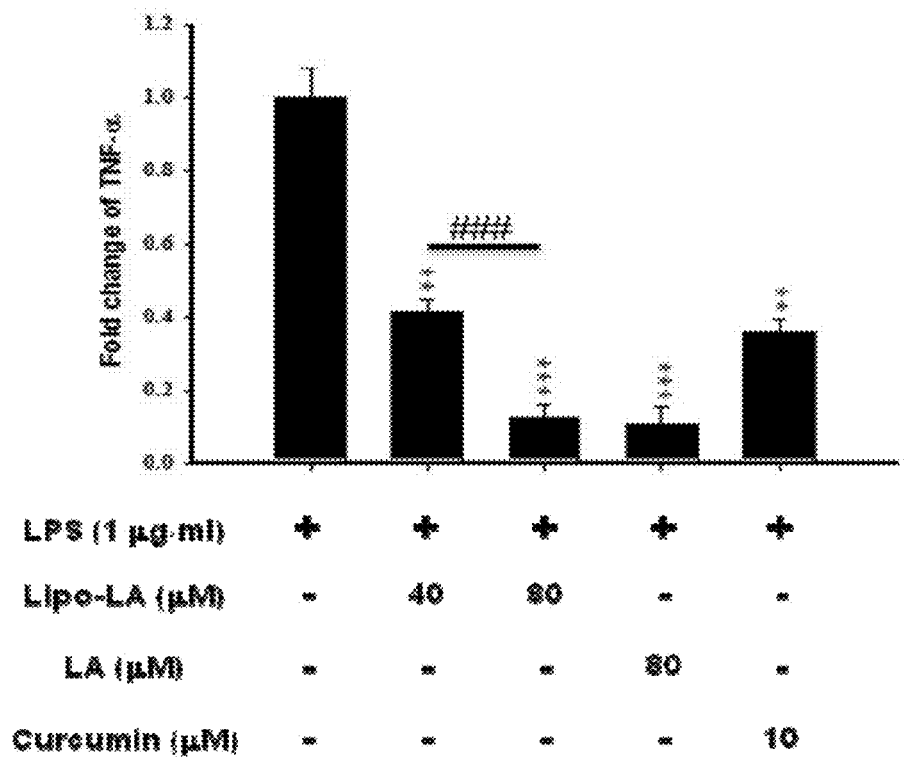
Figure 4C:
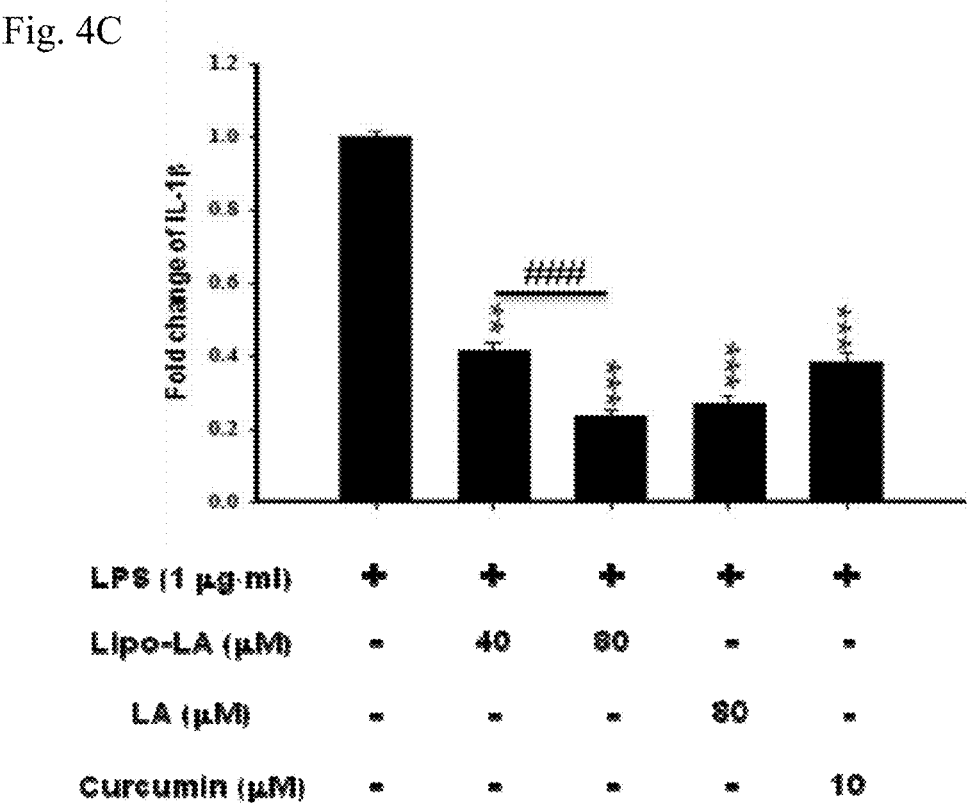
Figure 4D:
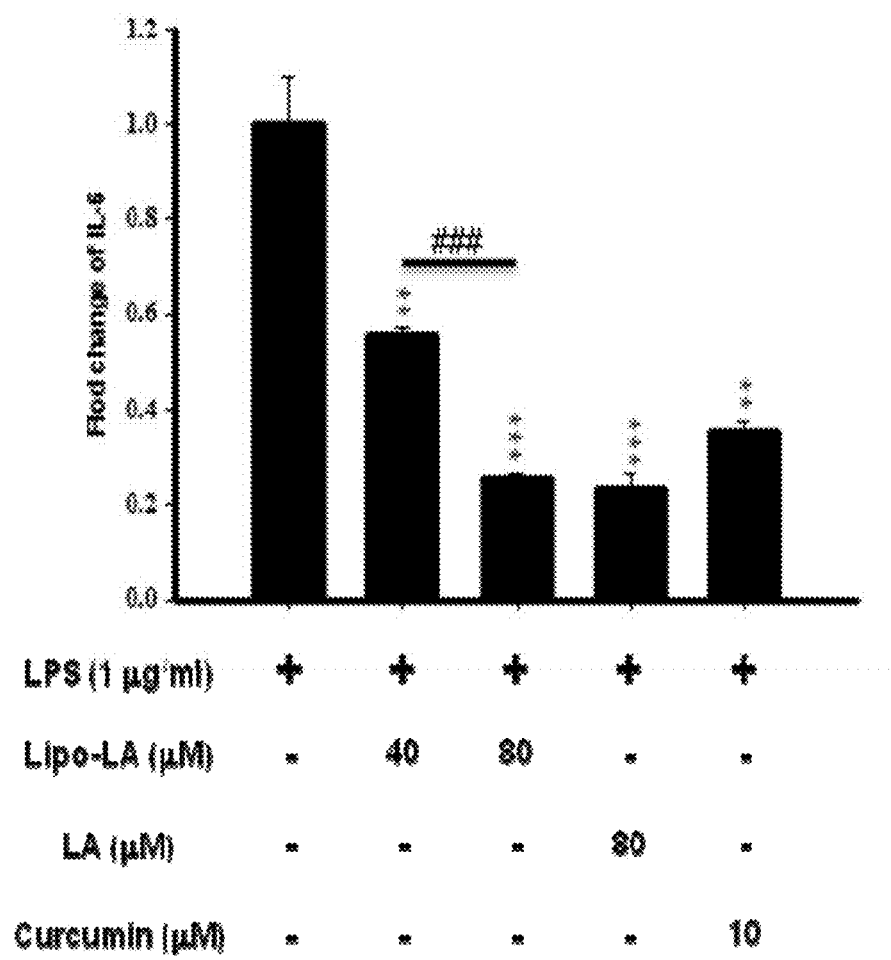

Next, the real time Q-PCR is used for analyzing the change of NFATc1 (nuclear factor of activated T cell, the major factor of osteoclast proliferation and known as cytoplasmic 1) under the RANKL induction and drug treatments. As shown in FIG. 3B, the expression level of transcriptional factor NFATc1 is increased by the stimulation of RANKL, and is significantly reduced after the treatment of drugs.

Suppression of the Inflammatory Mediator Production by the Treatment of Liposomal Lupeol Acetate (Lipo-LA)

Proinflammatory cytokines can be released by activated macrophages, resulting in more activation of immune cells. For inhibition of inflammation study, LPS-stimulated RAW 264.7 cells (mouse leukaemic monocyte macrophage cell line) were treated with Lipo-LA, LA, and using curcumin as the positive control. In this experiment, 80 μM of each lipo-LA and LA is used for one hour treatment before the addition of 1 μg/ml of LPS to stimulate macrophages. After cultured for 24 hours, the supernatants for each group were collected, and the expression level of TNF-α, IL-1β and IL-6 is detected by ELISA.

As shown in FIG. 4, Lipo-LA effectively inhibits the release of TNF-α, IL-1β and IL-6 from the activated macrophages. The results of this experiment confirmed that Lipo-LA could effectively reduce inflammatory responses in RAW 264.7 cells.

Figure 5:
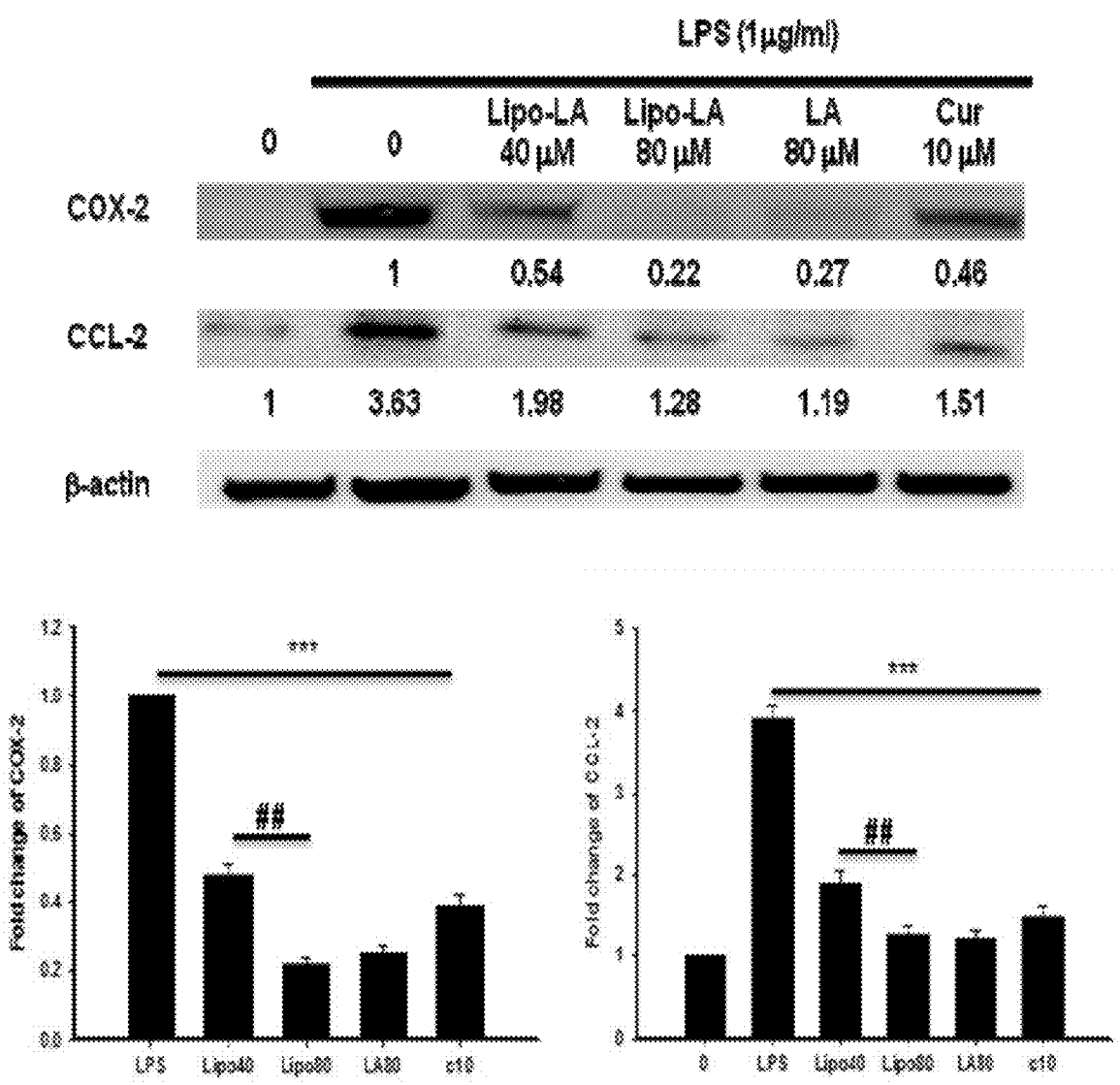
FIG. 5 shows the inhibitory effects of liposomal lupeol acetate (Lipo-LA) on the expression of cell migration-related proteins and NF-κB. After the one hour treatment of drugs and the cultivation with 1 μg/ml LPS for 24 hours, cells were harvested for analyzing the expression of COX-2 and CCL-2 (chemokine (C-C motif) ligand 2, also known as monocyte chemotropic protein-1, MCP-1) with Western blotting. ***$p<0.001$, in comparison to LPS group; ##$p<0.01$, the comparison between 40 μM Lipo-LA and 80 μM Lipo-LA.

In the LPS stimulation, causes of cell migration may be regulated by COX-2 and CCL-2 (MCP-1). Thus, Western blotting is used to investigate whether the expression levels of COX-2 and CCL-2 (MCP-1) is decreased after giving the Lipo-LA treatment. The results are shown in FIG. 5, indicating that the expression level of COX-2 and MCP-1 are indeed decreased in the Lipo-LA treated group, which confirmed that the inhibitory effects of Lipo-LA in cell migration is regulated by COX-2 and MCP-1.

Establishment of collagen-induced arthritis (CIA)-bearing animal model and use for estimating the therapeutic efficacy of Lipo-LA treatment.

The animal model used in present studies of rheumatoid arthritis is the collagen-induced arthritis animal model; the progression of rheumatoid arthritis in this animal model is similar to that in human. In this embodiment, bovine type II collagen combined with complete Freund's adjuvant (CFA) is used to induce rheumatoid arthritis in DBA/1J mice.

The type II collagen is a major component of cartilage, and the use of heterologous (bovine) collagen will induce the production of anti-CII antibody in mice, resulting in the self-immune response to attack its own joint cartilage. In the early stage, the complement system is initially activated to attract neutrophils and macrophages, and stimulate the release of inflammatory cytokines from the activated cells. The inflammatory mediators will further affect T cells, B cells and more macrophages to produce a more severe inflammation and further attack joints to progress into rheumatoid arthritis.

In this embodiment, eight-week-old DBA/1J mice (purchased from Jackson Lab and propagated in the Animal Center of National Yang-Ming University, using a reproductive way of one male and two female mice) are used. 100 μl of arthritis-inducing adjuvant is injected into the dermis of tail (intra-dermal, id.) using a 30 G syringe; and a 50 μl second dose of same ingredients is injected in the same way at an interval of 21 days. The symptoms are produced at about six days after the second dose injection, with an induction rate of 100%. The arthritis-inducing adjuvant contain bovine collagen type II (CII, Cat. 20022, Chondrex, USA) dissolved in Complete Freund's Adjuvant (CFA, Cat. 7023, Chondrex, USA) containing 5 mg/ml of TB bacteria *M. Tuberculosis* H-37 RA at an equal proportion by using a homogenizer.

The paw swelling of mouse is evaluated with expressions in five phases 0, 1, 2, 3 and 4, with the highest score of 16 points in each mouse. The fore legs and hind limbs of the mice were observed three times a week after the second dose injection of arthritis-inducing adjuvant; for the stage 0=normal joint, 1=one swelling joint appeared, 2=more than one joint swelling phenomenon appeared, 3=swelling phenomenon appeared on the whole paw, and 4=very severe swelling appeared from the paw to the ankle. After the injection of the second dose of arthritis-inducing adjuvant, the central thickness of hind paw is measured and recorded three times a week using a digital caliper. The incidence of rheumatoid arthritis is started at 4-7 days after the injection of the second dose of arthritis-inducing adjuvant, that is the $25^{th}$ to $28^{th}$ day of the experiment.

Figure 6A:
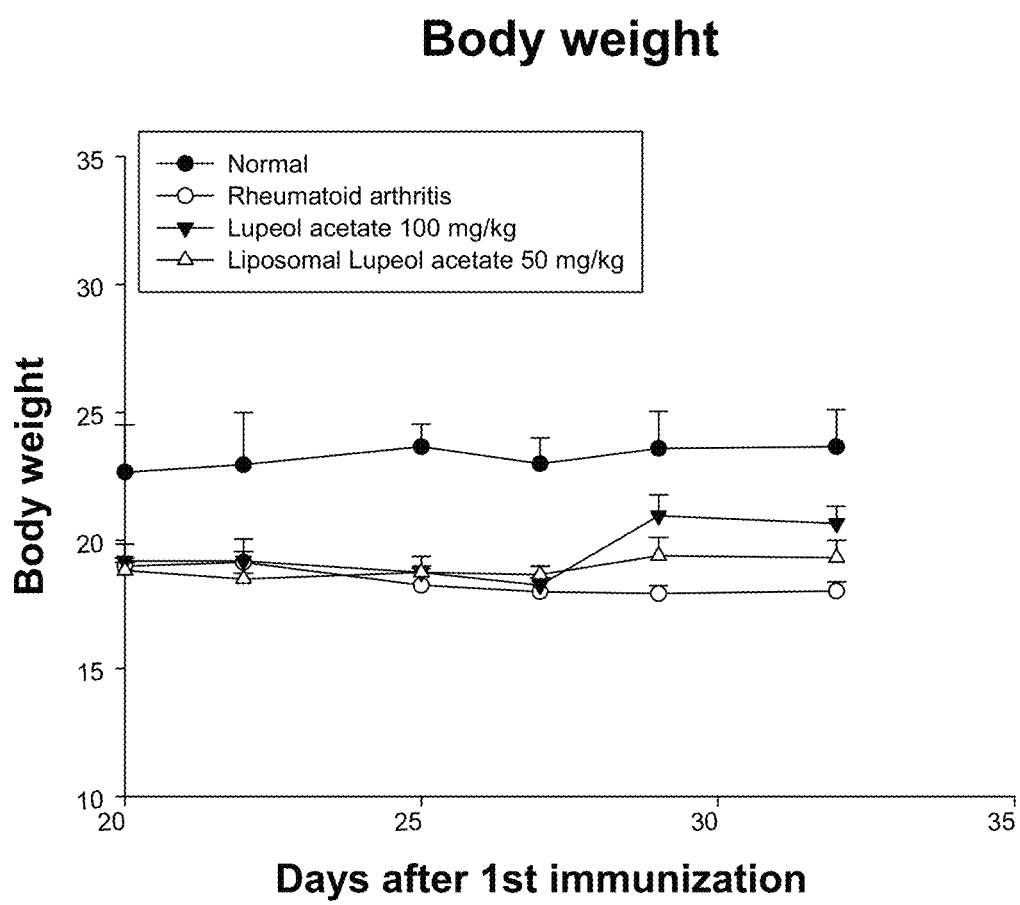
FIGS. 6A-6D show the evaluation of therapeutic efficacy of Lipo-LA treatment in the CIA-induced RA animal model.
Figure 6B:
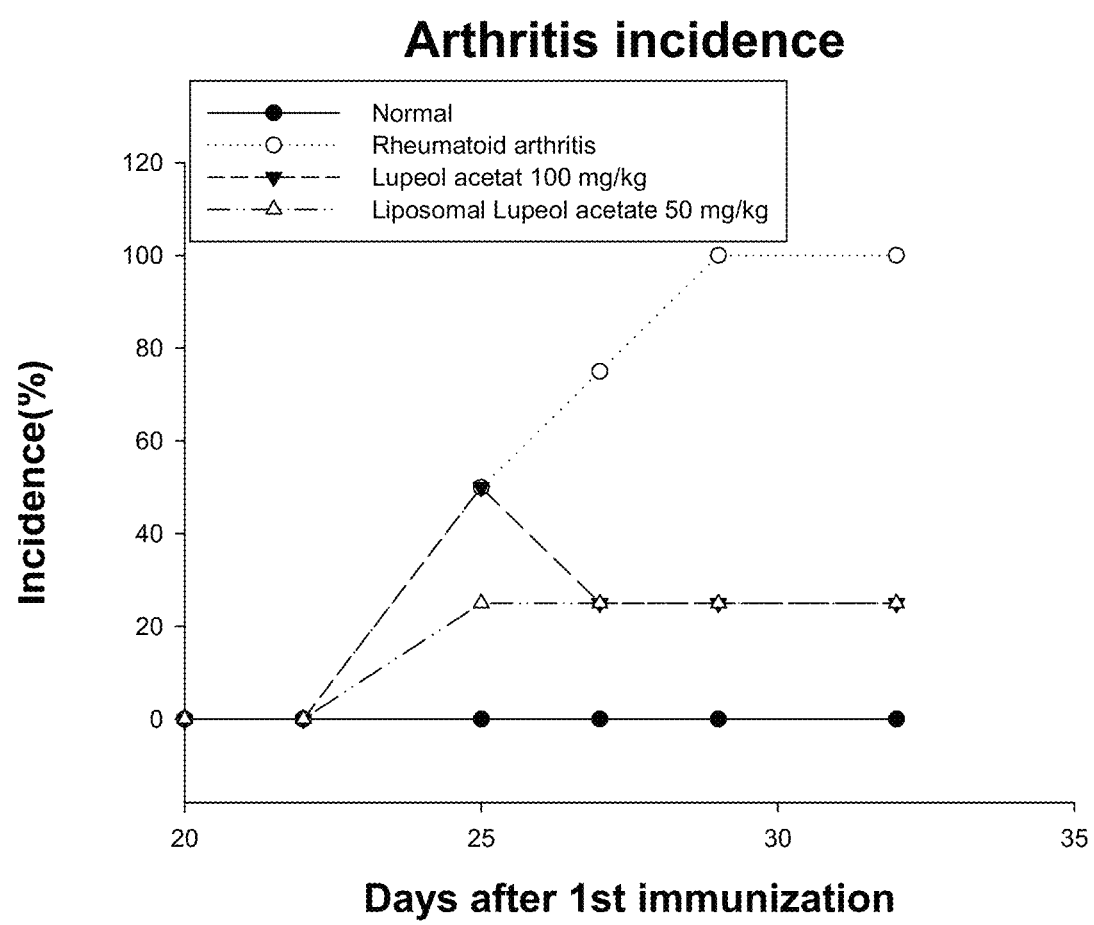
Figure 6C:
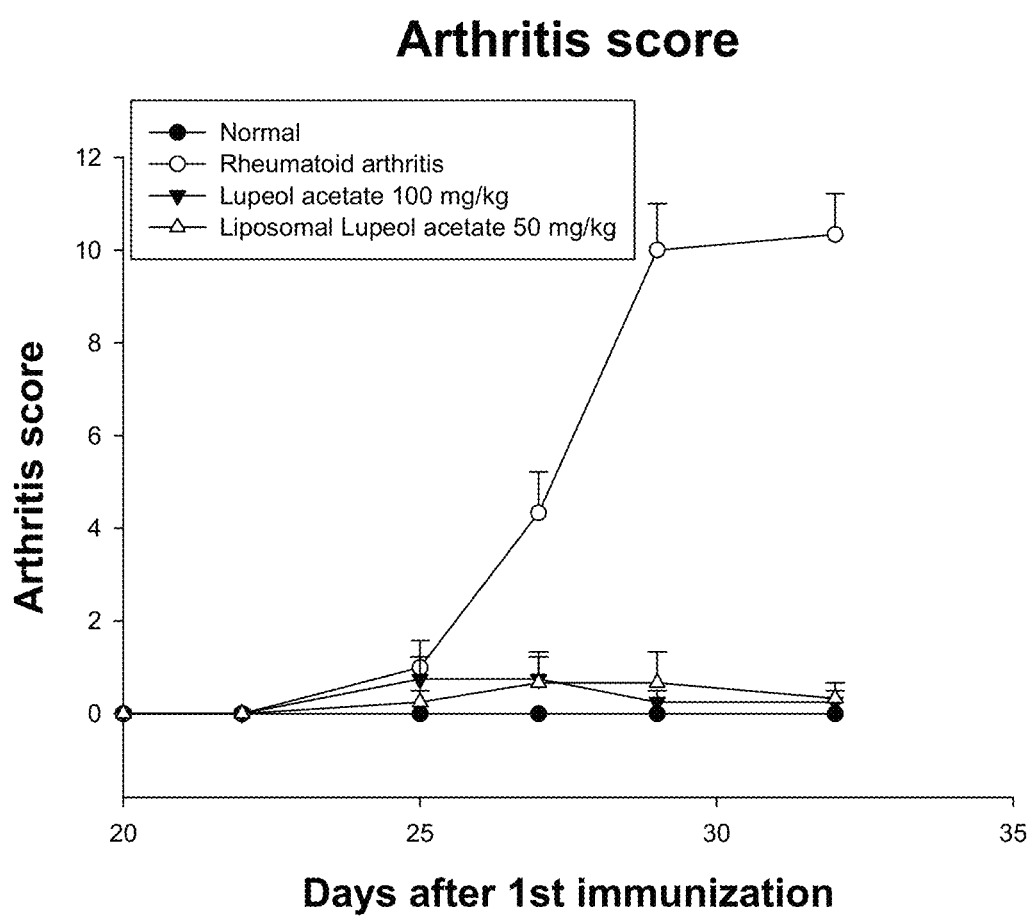
Figure 6D:
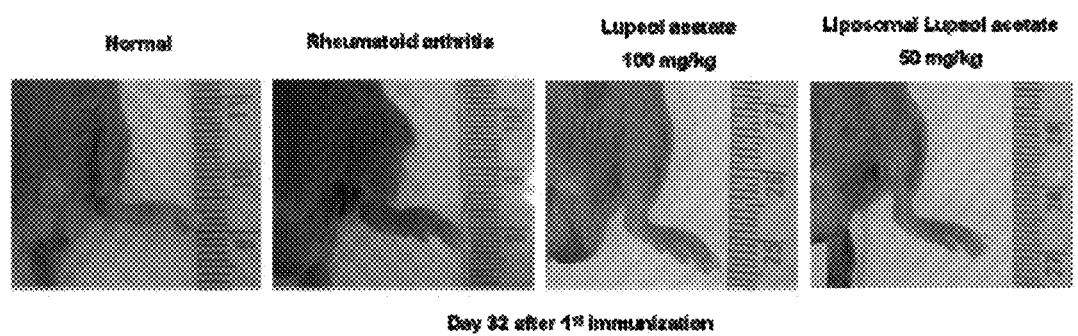
Figure 6D:
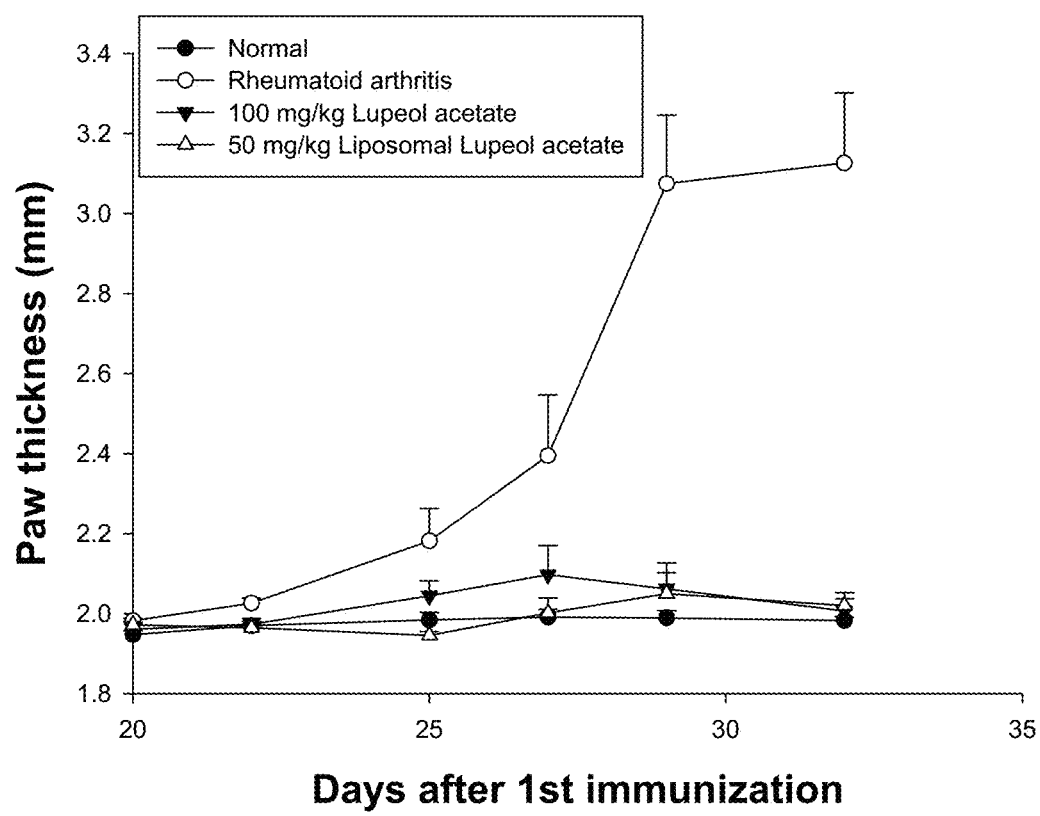

The DBA/1J mice were randomly divided into four groups (n=5 for each group): (1) normal mice group treated with deionized distilled water (ddH$_2$O) containing 0.1% dimethyl sulfoxide (DMSO, Sigma, USA); (b) rheumatoid arthritis (RA) mice group; (c) LA treated groups: orally administered with continuous daily feeding of a solution containing 100 mg/kg lupeol acetate in 0.1% dimethyl sulfoxide (DMSO, Sigma, USA); and (d) Lipo-LA treated groups: orally administered with continuous daily feeding of a solution containing 50 mg/kg liposomal lupeol acetate in 0.1% dimethyl sulfoxide (DMSO, Sigma, USA) until the end of the experiment (on the $32^{nd}$ days and $43^{th}$ day). The experiments were repeated three times, and one of the representative was shown. FIG. 6D (top panel) shows the paw swelling of the representative mouse in each animal group. In the progression, the body weight change of mice in all groups shows insignificant changes (within 20%), indicating that the drug does not have cytotoxicity on mice (see FIG. 6A).

The incidence of arthritis and the swelling score of paws in each group are also tracked for the entire experiment, showing that the foot swelling of both LA- and Lipo-LA treated mice is significantly reduced, as the evaluated swelling score of swollen feet and the swelling phenomenon appeared on foot both are obviously improved, when compared to the mice in RA group. From the results as shown in FIG. 6B to FIG. 6D, it is indicated that half dosage of Lipo-LA (50 mg/kg vs. 100 mg/kg of LA) can alleviate the condition of arthritis, and there are significant differences in the therapeutic efficacy between the groups of Lipo-LA treated mice and arthritis mice. In the serum analysis, the levels of TNF-α, IL-1β, IL-6 and IL-17 as measured in the previous experiment were significantly decreased, and the concentrations of cytokines in the blood of RA mice showed the same trend with the onset scores and foot swelling measured by digital caliper, all reached to the highest point on the $32^{nd}$ day of the experiment.

Lipo-LA Inhibits the Expression of RA-Related Proteins and Reduces the Activity of NF-κB.

The mice were sacrificed by cervical dislocation on the $32^{nd}$ day of the animal experiment. The whole leg of mouse was removed, and the leg tissue was ground by adding an appropriate amount of lysis buffer (tissue protein extraction reagent, T-PER, Pierce Protein Biology Products, IL, USA), centrifuged at 15,000 rpm for 20 minutes, and the supernatant is taken as the sample for each group.

The LightShift Chemiluminescent. EMSA kit (Pierce, Rockford, Ill., USA) is used in the analysis for NF-κB/DNA binding activity. Nuclear extracts were incubated with the biotin labeled DNA probes at room temperature for 20 minutes. The separated DNA/protein complexes from the free oligonucleotide on 10% polyacrylamide gel were transferred to a nylon membrane. The nylon membrane was immersed in ECL (Pierce, Rockford, Ill., USA) and reacted to emit cold light (luminescence), and then exposed to the film for the observation of NF-κB activity. Using IMAGE J software (National Institutes of Health), the obtained images were quantified to blackening degree, the blackening degree of the protein to be observed is divided by the value obtained in the control group to compare the differences of each group in the expression level of nuclear proteins.

Treg cell is an immunosuppression-related T cell, and usually less differentiated in autoimmune diseases. Some literatures have indicated that the back injection of Treg cells to mice will effectively reduce the incidence of rheumatoid arthritis. Therefore, we implicate that the increase in the number of Treg cells induced by the treatment of the Lipo-LA can reduce the occurrence of rheumatoid arthritis.

Figure 7A:
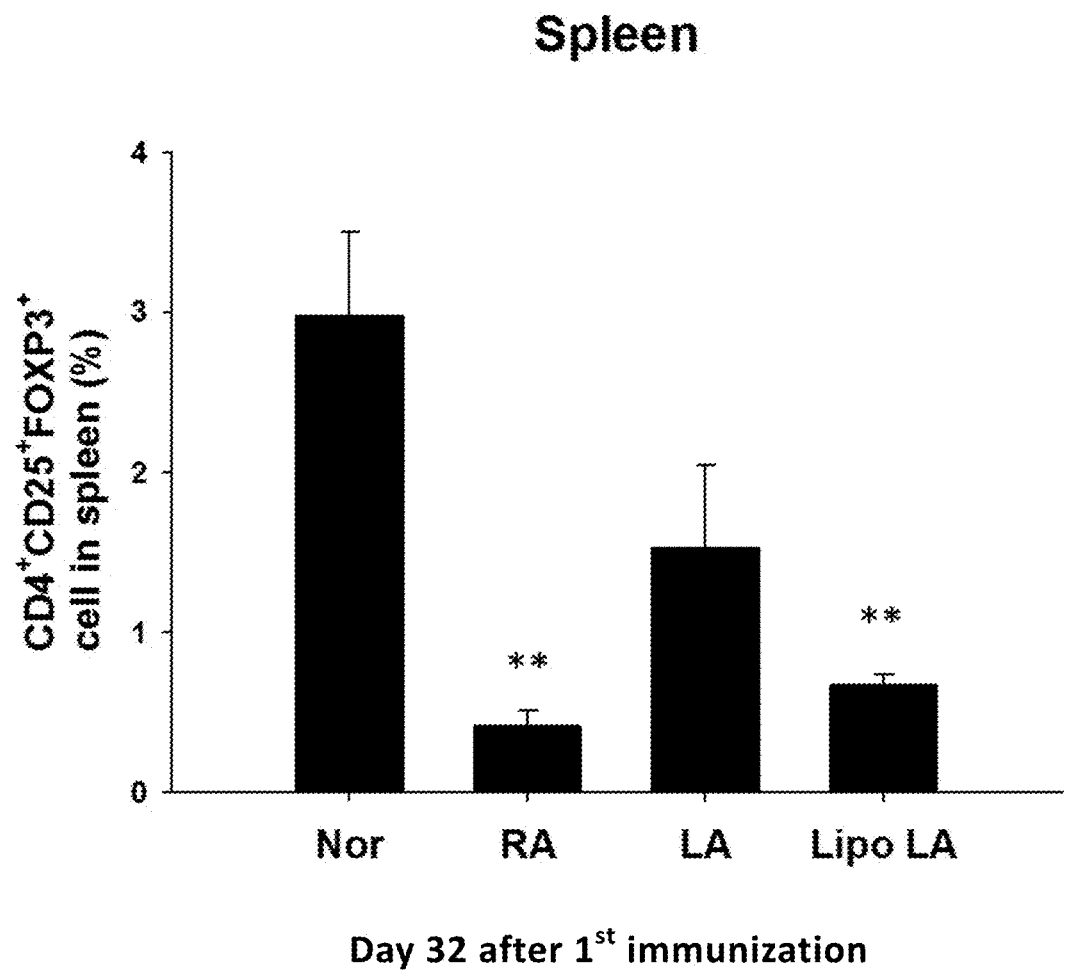
FIGS. 7A-7D show the increased expression of Treg and reduced expression of NF-κB and RA-related proteins in 50 mg/kg Lipo-LA treated mice. Mice were sacrificed at the $32^{nd}$ day of animal experiment, and the spleen and inguinal lymph nodes were removed for the Treg analysis as shown in FIG. 7A and FIG. 7B, respectively.
Figure 7B:
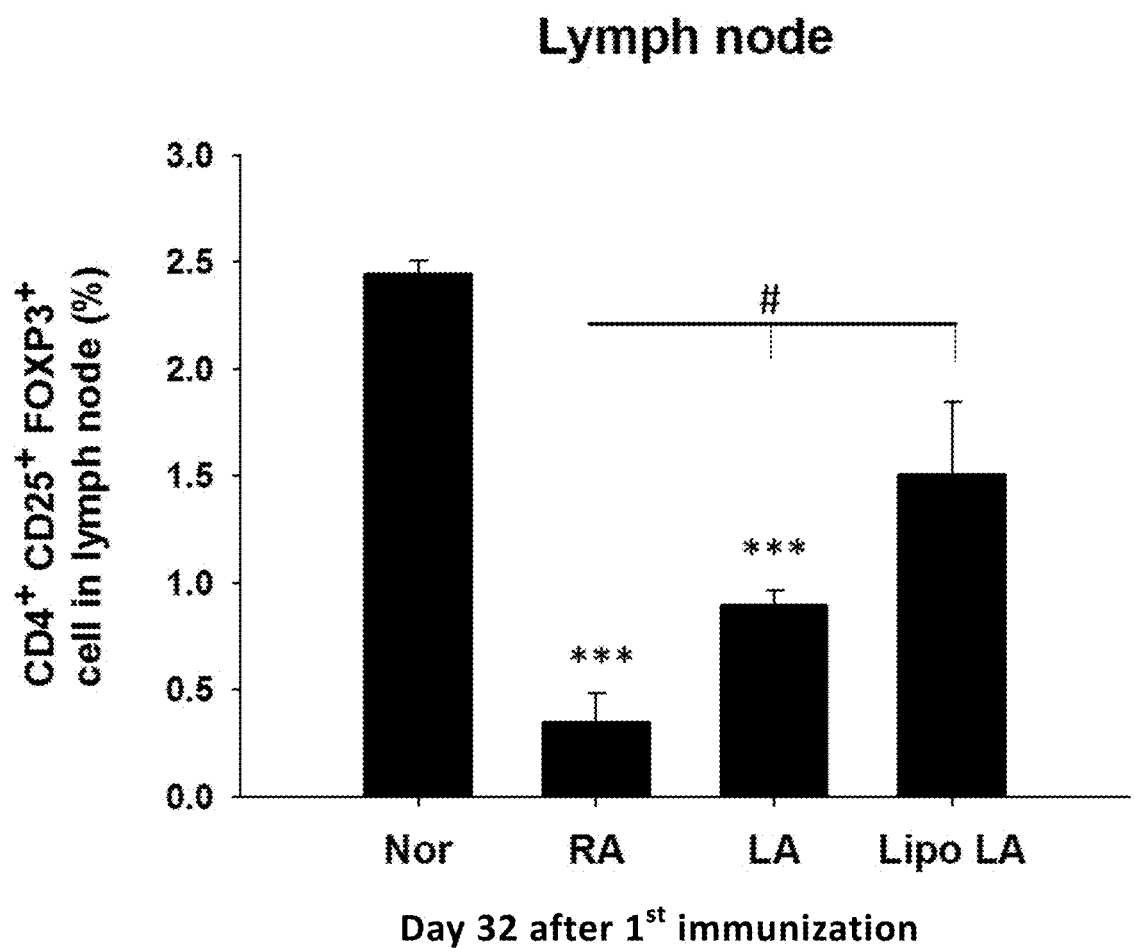

The mice were sacrificed at the peak of the incidence, that is the $32^{nd}$ day of the experiment, and the spleen and inguinal lymph nodes were removed for the Treg cell analysis. The results of the experiment showed that the Treg differentiation in the inguinal lymph nodes was increased in the Lipo-LA treated groups, which has achieved a significant difference comparing with the rheumatoid arthritis (RA) group (see FIG. 7A-B). Meanwhile, we also use Western blotting to observe the proteins extracted from mouse hind legs, and observe the expression level of immunosuppression-related proteins TGF-β and IL-10 secreted from Treg cells. The results shown in FIG. 7C indicate that both of the levels of immunosuppressive factors TGF-β and IL-10 secreted by the Treg in the 100 mg/kg LA and 50 mg/kg Lipo-LA treated groups display a rising trend.

Figure 7C:
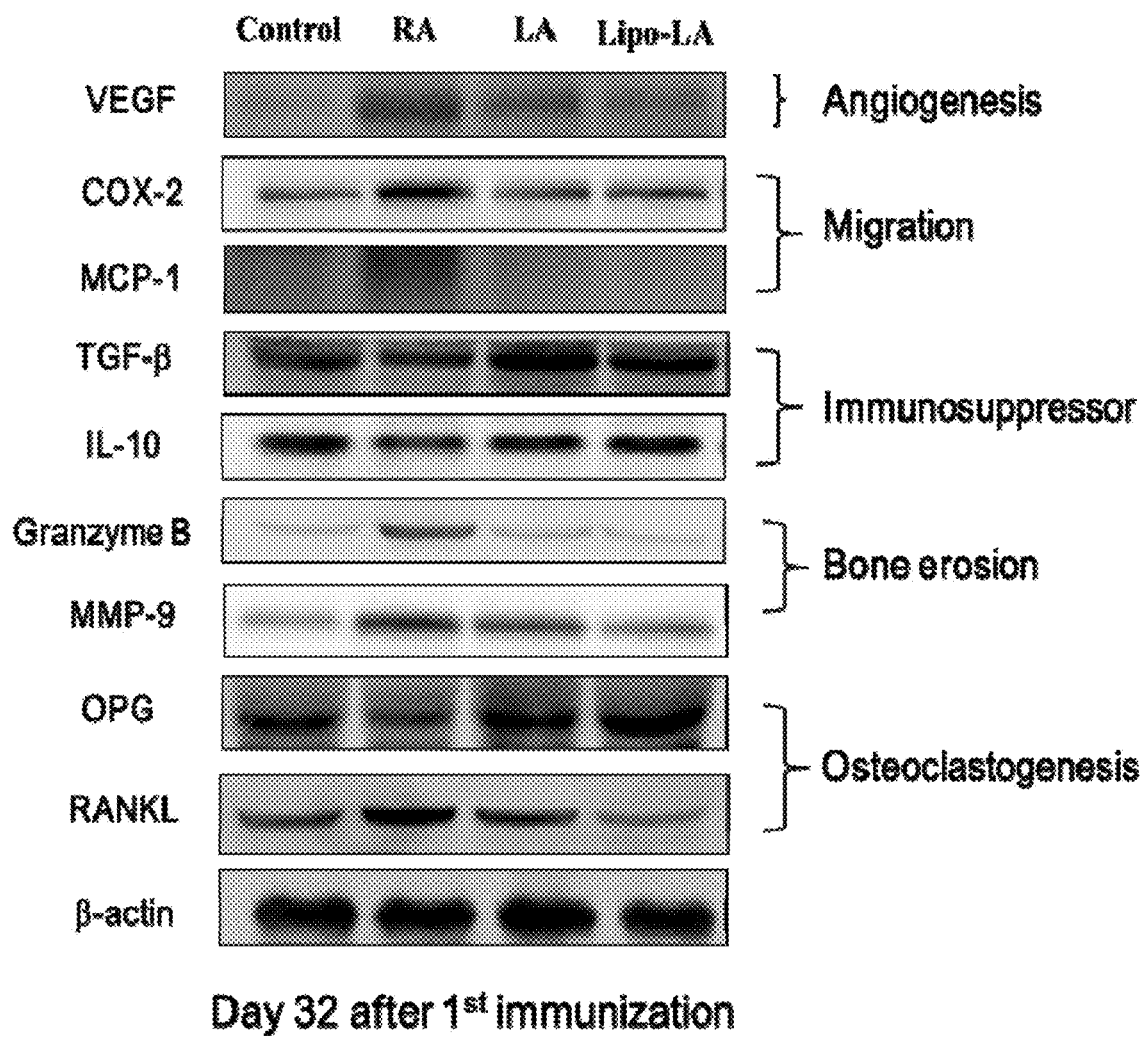
Figure 7D:
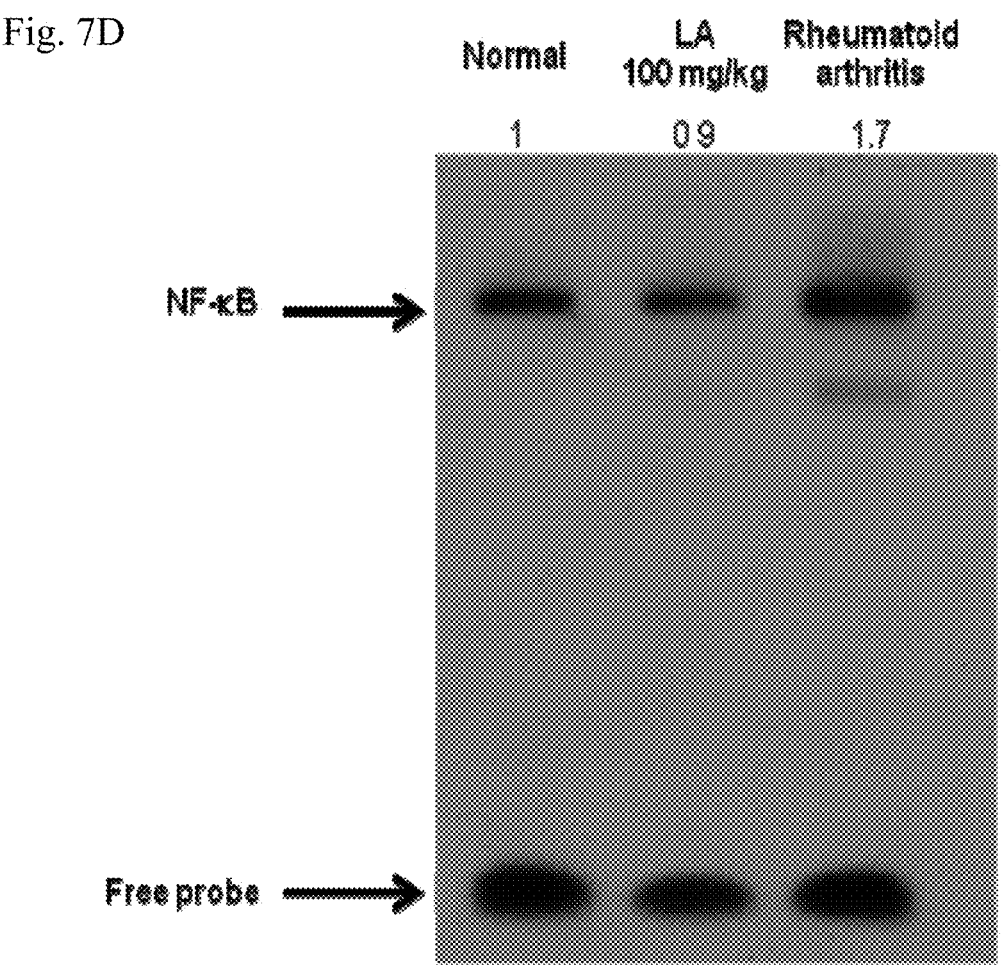

As shown in FIGS. 7C and 7D, in the Lipo-LA treated group the VEGF (angiogenesis) is indeed reduced; the expression levels of cell migration-related proteins COX-2 and MCP-1 are also reduced; the suppression of the expression of bone disintegration causing proteins not only inhibits the bone erosion of granzyme B, but also the expression of cartilage damage causing protein matrix metalloproteinase-9 (MMP-9) released by cartilage cells and fibroblasts; and the expression of regulatory factors for the generation of osteoclast and osteoblasts RANKL (receptor activator of nuclear factor NF-κB ligand) and OPG (Osteoprotegerin) is reduced and increased, respectively, when compared to the RA group. The observation of the changes in NF-κB expression by EMSA showed a recovery of NF-κB expression to the same level as that of normal mice after treating with Lipo-LA, indicating that the expression of NF-κB is inhibited by the treatment of Lipo-LA, as comparing to the RA group where the NF-κB expression is much higher than the other two groups. From the results described above, it is suggested that Lipo-LA inhibits the formation, maturation and proliferation of osteoclasts by regulating the level of NF-κB expression.

Observing the suppressive effects of Lipo-LA on joint inflammation using immunohistochemistry (IHC). The mice were sacrificed by cervical dislocation on the 43$^{rd}$ day of the animal experiment. The legs of mouse were removed and subjected to paraffin embedding and sectioning. The sections were stained with anti-TNF-α and anti-IL-1β antibodies, respectively to assess the distribution of inflammatory cytokines.

Figure 8A:
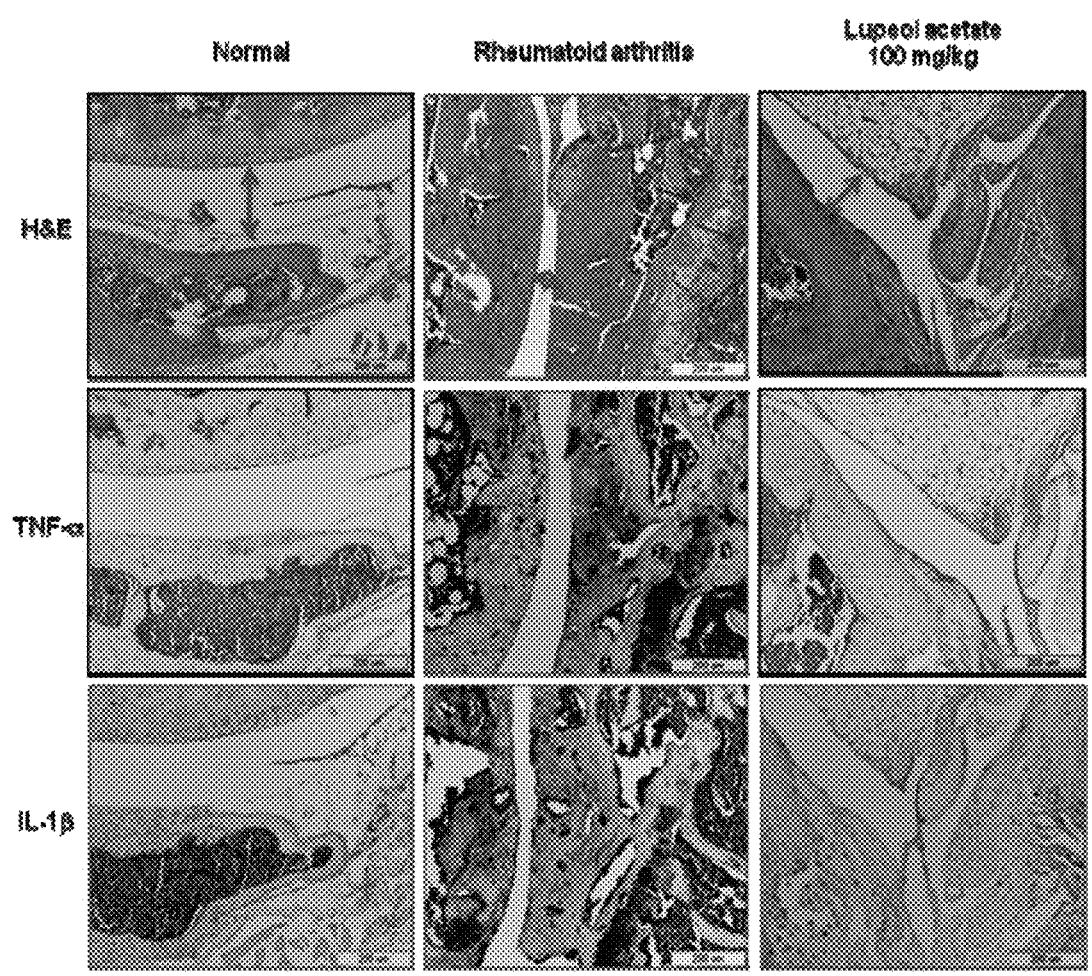
FIGS. 8A-8B show the improvements of joint swelling and the secretion of proinflammatory cytokines TNF-α and IL-1β in RA mice by the treatments of 100 mg/kg LA and 50 mg/kg Lipo-LA.
Figure 8B:
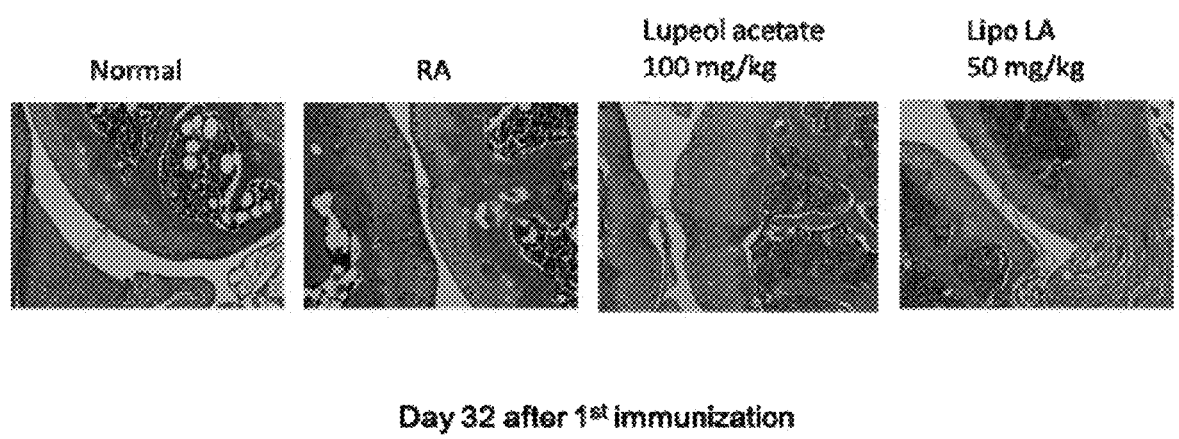

From the results of H & E staining shown in FIG. 8, it is indicated that the articular cavity in the mouse of RA group is significantly smaller than that in the animal of Lipo-LA treated group, and the joint surface is less flat in the mouse of RA group. In the TNF-α and IL-1β staining, it is also clearly observed that mice in RA group exhibit greater infiltration of cytokines. And from the immunohistochemistry images of TNF-α and IL-1β staining, there is a significantly less cytokine profile in Lipo-LA treated group. The above results confirm that Lipo-LA can effectively maintain the shape of articular cavities, and reduce the infiltration of inflammatory cytokines.

In summary of the experimental results described above, it has proven that lupeol acetate liposome (so called Liposomal-LA) can alleviate the inflammatory response by inhibiting the release of cytokines, such as Cox-2, MCP-1, TNF-α, IL-1β and the like by macrophages, and reduce the expression of osteoclastogenesis-related proteins, such as MCP-1, Cox-2, granzyme B, MMP-9, TGF-β, IL-1β, OPG and RANKL by regulating the levels of NF-κB and NFATc1. The liposomal lupeol acetate can reach the same inhibitory effects on inflammation and osteoclastogenesis at a half dose of the un-coated LA. It had demonstrated in the in vivo animal experiments that the liposomal lupeol acetate of the present invention can effectively alleviate the joint inflammation, swelling, bone erosion and the incidence of rheumatoid arthritis in mice.

Moreover, the present invention is the first disclosure to confirm the inhibitory effects of lupeol acetate and liposomal lupeol acetate on osteoclast formation (osteoclastogenesis). By the revelation of present invention, lupeol acetate and liposomal lupeol acetate can not only be used for the treatment or prevention of rheumatoid arthritis, but also to treat or prevent osteoporosis, reduce the joint deformity arising from the destruction in periarticular bone by osteoclasts, and maintain the integrity of articular surface, which is also an innovation of the invention.

In addition, the current therapy of rheumatoid arthritis is often in combination with steroid drugs, which will increase the chance of occurring side effects such as osteoporosis. Therefore, the present invention provides a composition comprising liposomal lupeol acetate combined with conventional steroids for the treatment of rheumatoid arthritis, which is beneficial to reduce the probability and severity of osteoporosis in the patients with rheumatoid arthritis by the effects on inhibiting osteoclast generation.

The invention claimed is:
1. A pharmaceutical composition comprising:
 a liposomal lupeol acetate for use of inhibiting osteoclastogenesis;
 wherein the liposomal lupeol acetate consists of:
  lupeol acetate;
  an aqueous core; and
  a lipid bilayer having an inner space in which the lupeol acetate is located is constructed by a phosphatidylcholine (PC) and polyethylene glycol-distearoylphosphatidylethanolamine (PEG-DSPE) and wherein the molecular ratio of the phosphatidylcholine and polyethylene glycol-distearoylphosphatidylethanolamine is 20:1 to 35:1.
2. The pharmaceutical composition of claim 1, wherein the phosphatidylcholine comprises egg phosphatidylcholine (EPC).
3. The pharmaceutical composition of claim 1, wherein the molecular ratio of the phosphatidylcholine (PC) and polyethylene glycol-distearoylphosphatidylethanolamine (PEG-DSPE) in the lipid bilayer is 30:1.
4. The pharmaceutical composition of claim 1, further comprising a steroid anti-inflammatory agent.
5. The pharmaceutical composition of claim 4, wherein the liposomal lupeol acetate is used to reduce osteoporosis caused by the steroid anti-inflammatory agent.

\* \* \* \* \*